(12) United States Patent
Murray et al.

(10) Patent No.: US 7,199,281 B2
(45) Date of Patent: Apr. 3, 2007

(54) METHOD OF GENERATING A TRANSGENIC LIVESTOCK ANIMAL

(75) Inventors: James D. Murray, Davis, CA (US); Elizabeth A. Maga, Sacramento, CA (US); Gary B. Anderson, Davis, CA (US); Stefanie M. Oppenheim, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 412 days.

(21) Appl. No.: 10/238,042

(22) Filed: Sep. 6, 2002

(65) Prior Publication Data

US 2003/0115618 A1    Jun. 19, 2003

Related U.S. Application Data

(60) Provisional application No. 60/317,915, filed on Sep. 7, 2001.

(51) Int. Cl.
*C12N 15/00* (2006.01)
*A01K 67/027* (2006.01)

(52) U.S. Cl. .............................. 800/25; 800/14; 800/15; 800/16; 800/17

(58) Field of Classification Search ..................... None
See application file for complete search history.

(56) References Cited

U.S. PATENT DOCUMENTS

| | | | |
|---|---|---|---|
| 5,763,240 A | 6/1998 | Zarling et al. | |
| 5,948,653 A | 9/1999 | Pati et al. | |
| 6,074,853 A | 6/2000 | Pati et al. | |
| 6,200,812 B1 | 3/2001 | Pati et al. | |
| 6,255,113 B1 | 7/2001 | Zarling et al. | |

FOREIGN PATENT DOCUMENTS

WO    WO 99/60108    11/1999

OTHER PUBLICATIONS

Maga, E. The use of recombinase proteins to generate transgenic large animals, Cloning and Stem Cells, 3:233-241, 2001.*
Niemann, 1997, Transg. Res. vol. 7, pp. 73-75.*
Kilby, 1993, Trends in Genetics, 9:413-421.*
Moreadith, 1997, Gene targeting in embryonic stem cells : the new physiology and metabolism, Journal of Molecular Medicine, vol. 75, pp. 208-216.*
Seamark, 1994, Reproductive Fertility and Development, 6:653-7.*
Mullins, 1996, J. Clin. Invest., vol. 98, pp. S37-S40.*
McCreath, 2000, Nature, vol. 405, pp. 1066-1069.*
Denning, C. 2001A, Nature Biotechnology, vol. 19, pp. 559-562.*
Dinnyes, 2002, Cloning and Stem Cells, vol. 4, pp. 81-90.*
Denning, C., 2001B, Gene Targeting from primaty fetal fibroblasts from sheep and pig, Cloning and Stem Cells, 3:221-231.*
Poljaeva, I.A., 2000, Nature, 407:86-90.*
Clark, A.J., 2000, Gene targeting in livestock: a preview, Transgenic Research, 9:263-275.*
Capecchi, 1994, Targeted Gene Replacement, Scientific American, vol. 270, pp. 34-41.*
http://en.wikipedia.org/wiki/Livestock.*
Harrison, SJ et al., 2002, Efficient generation of 1(1,3) galactosyltransferase knockout porcine fetal fibroblasts for nuclear transfer, Transgenic Research, 11:143-150.*
Poljaeva I.A.and Campbell, KHS, 2000, New advances in somatic cell nuclear transfer:application in transgenesis, Theriogenology, 53:117-126.*
Thomson, AJ et al, 2003, Gene targeting in livestock, Reproduction Supplement, 61:495-508.*
Akhmedov et al. "Characterization of two nuclear mammalian homologous DNA-pairing activities that do not require associated exonuclease activity" *Proc. Natl. Acad Sci.USA* vol. 92, pp. 1729-1733, Feb. 1995.
Liu et al., "Insulin-Like Growth Factor-I Affects Perinatal Lethality and Postnatal Development in a Gene Dosage-Dependent Manner: Manipulation Using the Cre/loxP System In Transgenic Mice" *Molecular Endocrinology* (1998), vol. 12, No. 9, 1452-1462.
Plug et al., "Presynaptic associate of Rad51 protein with selected sites in meiotic chromatin" *Proc. Natl. Acad. Sci. USA* vol. 93, pp. 5920-5924, Jun. 1996.
Utomo, A.R.H. "Temporal, Spatial, and Cell Type Specific Control of Cre-Mediated DNA Recombination in Transgenic mice" *Nature Biotechnology*, Nov. 1999, vol. 17, 1091-1098.

* cited by examiner

*Primary Examiner*—Valarie Bertoglio
(74) *Attorney, Agent, or Firm*—Paula A. Borden; Bret Field; Bozicevic, Field & Francis

(57) ABSTRACT

The present invention provides methods of producing transgenic livestock animals. The methods generally involve first introducing a nucleoprotein made up of nucleic acid and a recombinase into a totipotent or pluripotent cell to produce a recombinant totipotent or pluripotent cell and then growing the recombinant totipotent or pluripotent cell to produce the transgenic livestock animal. The invention further provides kits for use in generating transgenic non-human animals of the invention.

8 Claims, 3 Drawing Sheets

M 1 2 3 4 5 6 7 θ - c i M

M 1 2 3 4 5 6 7 8 9 10 11 θ - - i M 1 2 3 4 5 6 7 8
M u e u e u e u e u e u e u e θ - mm M

M 1 2 3 4 5 6 7 8 θ - m +

SEQUENCE LISTING

<160> NUMBER OF SEQ ID NOS: 28

<210> SEQ ID NO 1
<211> LENGTH: 30
<212> TYPE: DNA
<213> ORGANISM: Goat

<400> SEQUENCE: 1
aaatggtacc ggggcccggg gatgagccaa                30

```
<210> SEQ ID NO 2
<211> LENGTH: 30
<212> TYPE: DNA
<213> ORGANISM: Goat

<400> SEQUENCE: 2
aaattctaga tgaggcccag ctcccctgcc                               30

<210> SEQ ID NO 3
<211> LENGTH: 13
<212> TYPE: DNA
<213> ORGANISM: goat

<400> SEQUENCE: 3
gcggccgctc gag                                                 13

<210> SEQ ID NO 4
<211> LENGTH: 32
<212> TYPE: DNA
<213> ORGANISM: goat

<400> SEQUENCE: 4
gcggccgctc gagggctgca gctggggtcg tg                            32

<210> SEQ ID NO 5
<211> LENGTH: 33
<212> TYPE: DNA
<213> ORGANISM: goat

<400> SEQUENCE: 5
ctcgagcggc cgcaagtgcc tcctgcttgc cct                           33

<210> SEQ ID NO 6
<211> LENGTH: 28
<212> TYPE: DNA
<213> ORGANISM: goat

<400> SEQUENCE: 6
ctcgagatga tgaagagttt tttcctag                                 28

<210> SEQ ID NO 7
<211> LENGTH: 25
<212> TYPE: DNA
<213> ORGANISM: goat

<400> SEQUENCE: 7
ctcgagttta ttatgcagga atcaa                                    25

<210> SEQ ID NO 8
<211> LENGTH: 19
<212> TYPE: DNA
<213> ORGANISM: pig

<400> SEQUENCE: 8
tagtggatcc aggcctgtc                                           19

<210> SEQ ID NO 9
<211> LENGTH: 21
<212> TYPE: DNA
<213> ORGANISM: pig

<400> SEQUENCE: 9
gatagagctg ggtcctctgc g                                        21
```

<210> SEQ ID NO 10
<211> LENGTH: 52
<212> TYPE: DNA
<213> ORGANISM: pig

<400> SEQUENCE: 10
cacgaggtgt agtggatcca ggcctgtcga cttcctcttc tgcattgacg tg    52

<210> SEQ ID NO 11
<211> LENGTH: 22
<212> TYPE: DNA
<213> ORGANISM: Pig

<400> SEQUENCE: 11
aatgtaggct gcggactcct tc    22

<210> SEQ ID NO 12
<211> LENGTH: 51
<212> TYPE: DNA
<213> ORGANISM: Pig

<400> SEQUENCE: 12
gaggaagacg tcgacaggcc tggatccact acacctcgtg ctggatgtgg g    51

<210> SEQ ID NO 13
<211> LENGTH: 52
<212> TYPE: DNA
<213> ORGANISM: Pig

<400> SEQUENCE: 13
ggatccgttt tcccagtcac gacgcatgcc aggaaacagc tatgacaggc ct    52

<210> SEQ ID NO 14
<211> LENGTH: 20
<212> TYPE: DNA
<213> ORGANISM: goat

<400> SEQUENCE: 14
aggcctccta ttgtcctcgt    20

<210> SEQ ID NO 15
<211> LENGTH: 20
<212> TYPE: DNA
<213> ORGANISM: goat

<400> SEQUENCE: 15
acgtcacagc ctctcttggt    20

<210> SEQ ID NO 16
<211> LENGTH: 19
<212> TYPE: DNA
<213> ORGANISM: Goat

<400> SEQUENCE: 16
ccgggctggc tggctggca    19

<210> SEQ ID NO 17
<211> LENGTH: 22
<212> TYPE: DNA
<213> ORGANISM: goat

<400> SEQUENCE: 17

```
tcgaaccttc tggatgtcca gg                                              22

<210> SEQ ID NO 18
<211> LENGTH: 18
<212> TYPE: DNA
<213> ORGANISM: goat

<400> SEQUENCE: 18
cagccctcga gcggccgc                                                   18

<210> SEQ ID NO 19
<211> LENGTH: 20
<212> TYPE: DNA
<213> ORGANISM: goat

<400> SEQUENCE: 19
tgggaatgga tggctacagg                                                 20

<210> SEQ ID NO 20
<211> LENGTH: 20
<212> TYPE: DNA
<213> ORGANISM: goat

<400> SEQUENCE: 20
ctcaagctac agcatcagcg                                                 20

<210> SEQ ID NO 21
<211> LENGTH: 28
<212> TYPE: DNA
<213> ORGANISM: goat

<400> SEQUENCE: 21
ctcgagatga tgaagagttt tttcctag                                        28

<210> SEQ ID NO 22
<211> LENGTH: 26
<212> TYPE: DNA
<213> ORGANISM: goat

<400> SEQUENCE: 22
ctcgagttag accgcggttg aagtaa                                          26

<210> SEQ ID NO 23
<211> LENGTH: 21
<212> TYPE: DNA
<213> ORGANISM: pig

<400> SEQUENCE: 23
gagcattact tggaggagtt c                                               21

<210> SEQ ID NO 24
<211> LENGTH: 22
<212> TYPE: DNA
<213> ORGANISM: pig

<400> SEQUENCE: 24
gcctatatga taatcccagc ag                                              22

<210> SEQ ID NO 25
<211> LENGTH: 21
<212> TYPE: DNA
<213> ORGANISM: pig

<400> SEQUENCE: 25
```

```
gatagagctg ggtcctctgc g                                              21

<210> SEQ ID NO 26
<211> LENGTH: 19
<212> TYPE: DNA
<213> ORGANISM: pig

<400> SEQUENCE: 26
gacaggcctg gatccacta                                                 19

<210> SEQ ID NO 27
<211> LENGTH: 21
<212> TYPE: DNA
<213> ORGANISM: pig

<400> SEQUENCE: 27
gatagagctg ggtcctctgc g                                              21

<210> SEQ ID NO 28
<211> LENGTH: 51
<212> TYPE: DNA
<213> ORGANISM: pig

<400> SEQUENCE: 28
gaggaagacg tcgacaggcc tggatccact acacctcgtg ctggatgtgg g             51
```

METHOD OF GENERATING A TRANSGENIC LIVESTOCK ANIMAL

CROSS-REFERENCE TO RELATED APPLICATIONS

Pursuant to 35 U.S.C. § 119 (e), this application claims priority to the filing date of the U.S. Provisional Patent Application Ser. No.: (a) 60/317,915 filed Sep. 7, 2001; the disclosure of which are herein incorporated by reference.

INTRODUCTION

1. Field of the Invention

The field of this invention is transgenic non-human animals.

2. Background of the Invention

The overall goal in making a transgenic animal is the stable introduction of a desired DNA sequence into the germ line of the host animal that can be transmitted to offspring in a Mendelian fashion. By incorporating new or modified genes at the genetic level, the characteristics of the animal can be specifically changed. Transgenic animals are generated for a variety of purposes. They can be used as basic research models, specialized non-agricultural purposes (such as pharmaceutical production or xenotransplantation) and also to enhance animal production traits and products. For many applications, large animals, e.g., livestock such as pigs, cows, sheep, and goats, are of interest. Producing transgenic livestock is not as efficient as mice and is an expensive and time-consuming process. Accordingly, there is much interest in developing methods that increase the efficiency and specificity of the transgenic process in non-murine large animals.

Transgenic animals are generally produced by one of three main methods: 1) the pronuclear microinjection of fertilized one-cell embryos followed by reimplantation into surrogate mothers; 2) the genetic manipulation of embryonic stem (ES) cells followed by introduction of modified ES cells into developing embryos; and 3) by the genetic manipulation of somatic primary cells followed by nuclear transfer into a recipient oocyte. The standard and most established method of producing transgenic animals such as mice, rabbits, pigs, goats, or cows generally rely on the microinjection of DNA encoding a transgene into the pronucleus of fertilized zygotes. However, this method currently has several unavoidable shortcomings.

Pronuclear microinjection methods generally result in the random integration of transgenes in the chromosome of the zygote. If the DNA construct is integrated into an inactive region of chromosome, it is unlikely to be expressed. As a consequence, it is necessary to generate several founders and carry out extensive characterizations on them all in order to identify a line of animals that will stably express the transgene at appropriate levels. DNA construct design is also crucial when using pronuclear microinjection. Promoter and regulatory elements must be present in the DNA fragment injected in order to dictate when and where the transgene will be expressed. The optimization of transgene design is time consuming and labor intensive. When using pronuclear microinjection, only gene additions at a random location are feasible until recently. The complete removal, mutation or replacement of endogenous genes is not possible. Furthermore, the efficiency with which transgenic animals are generated with this technique is quite low.

Several of the problems discussed above can be circumvented by introducing DNA via the transfection of ES cells or by cloning, both of which allow for the targeted insertion of DNA into cells in culture. The important feature of these methods for the production of transgenic animals is that both ES cells or any donor cell (i.e., the differentiated somatic cell) to be used in nuclear transfer can be grown in culture and genetically modified with a desired transgene. The modified cells can then be selected, characterized prior to being used to generate transgenic animals. The potential advantages these methods offer over pronuclear microinjection include the ability to do gene targeting, thereby allowing for the creation of knockouts and enabling the modification of endogenous genes. Also, with cloning, all animals born will be germ line transgenic. However, identifying the homologous recombinants in a large population of non-homologous random integrants often proves to be the rate-limiting step for creating homologously modified mammalian cell lines. This severely limits the ability to manipulate target genes systematically.

These strategies are labor-intensive, time-consuming, and ultimately limit homologous recombination genetic engineering of mammalian cells for commercial applications. Other disadvantages include the fact that currently, among mammals, ES cells are available only for mice. While nuclear transfer allows for targeted modifications in livestock species, it is not supportive with all cell types, requires specialized techniques and conditions, is hard to maintain pregnancies and is associated with large offspring syndrome. Moreover, the process is also very inefficient. The efficiency and frequency with which transgenic animals are generated with these methods are in the same range as those of the more established and simpler method of pronuclear microinjection.

Presently, nuclear transfer efficiency in sheep is around 0.04–1.7% live born animals from reconstructed embryos, which is similar to standard pronuclear microinjection transgenic rates of approximately 1%.

Thus, there is a need in the art for methods of increasing the efficiency of generating transgenic animals, particularly livestock. The present invention addresses this need.

Literature

U.S. Pat. Nos. 5,763,240; 5,948,653; 6,074,853; 6,200,812; 6,255,113.

SUMMARY OF THE INVENTION

The present invention provides methods of producing transgenic livestock animals. The methods generally involve first introducing a nucleoprotein made up of nucleic acid and a recombinase into a totipotent or pluripotent cell to produce a recombinant totipotent or pluripotent cell and then growing the recombinant totipotent or pluripotent cell to produce the transgenic livestock animal. The invention further provides kits for use in generating transgenic non-human animals of the invention.

BRIEF DESCRIPTION OF THE FIGURES

(FIG. 2A) Identification of transgenic founders from the microinjection of RecA protein-coated cssDNA probe KCN. Lanes 1 and 2 are the umbilical and ear samples, respectively, and lane 7 is the umbilical from a known transgenic founder. Lanes 3–6 are ear samples from four negative animals. (FIG. 2B) Identification of transgenic pigs generated from the micorinjection of RecA protein-coated cssDNA probe Pig2 with primers GalT3/Mut2. Lanes 1 and 9 have the ear samples of two transgenic founders. The umbilical of one of the founders is negative (lane 8) and the umbilical and ears of four other pigs are negative (lanes 2–7 and 10–11). (FIG. 2C) Identification of transgenic goats from the microinjection of linear, double-stranded DNA construct $\alpha_{s1}$HLZ without RecA by PCR with primers HL3/HL4. The umbilical and ear of animal 6 is transgenic, all other animals are negative. (FIG. 2D) Identification of transgenic founders from the microinjection of conventional DNA construct $\alpha_{s1}$HLZ coated with RecA protein. Lanes 7 and 8 are the umbilical and ear samples from a transgenic founder. Lanes 1–6 are the umbilical and ear samples, respectively, from three non-transgenic goats.

DEFINITIONS

Figures 1A, 1B:
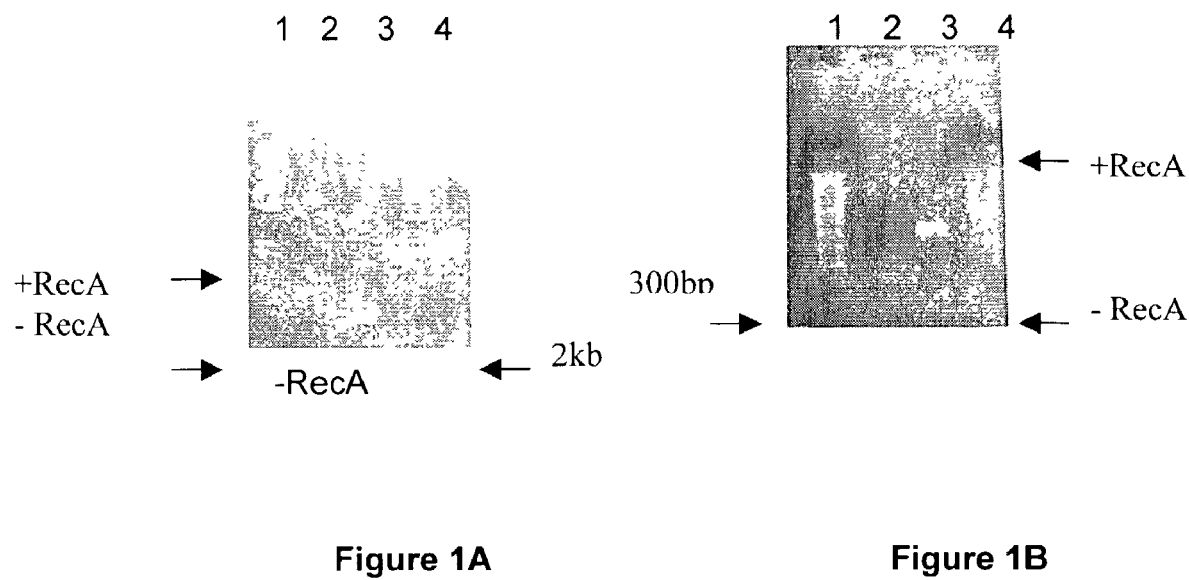
FIGS. 1A and 1B. RecA coating of goat and pig cssDNA probes. (1A) RecA coating of 2068 bp goat cssDNA probe KCNs. Lane 2: 100 ng of KCNs coated with RecA. Lane 3: 100 ng of double-stranded KCNs DNA (2068 bp). Lanes 1 and 4: λHindIII DNA marker. (1B) RecA coating of 304 bp pig cssDNA probe Pig1. Lane 2: 100 ng of Pig1 coated with RecA. Lane 3: 100 ng of double-stranded Pig1 DNA (304 bp). Lanes 1 and 4: 100 bp DNA marker. The mobility of the RecA-coated cssDNA is slowed compared to non-coated, double-stranded DNA.

The term "ungulate" is used to mean any species or subspecies of porcine (pig), bovine (cattle), ovine (sheep) and caprine (goats). In general the term encompasses hoofed farm animals (livestock). The terms "porcine" and "pig" are used interchangeably herein and refer to any porcine species and/or subspecies of porcine, and the same meaning applies to cows, sheep and goats.

A "mosaic animal" has cells of different genotypes. The term "mosaic animal" normally refers to animals with genetically distinct clones of cells derived from other cells in the animal. A mosaic animal could be an animal with clones of cells having undergone mitotic recombination.

A particular type of mosaic animal is a chimeric animal. The terms "chimera" and "chimeric animal" are used to describe an organism which includes genetic material from two different organisms arising from physical mixture of cells, e.g., from a physical mixture of produced by inserting embryonic stem cells from a first organism into early stage embryos (preimplantation embryos such as the blastocyst stage) of a second, different organism. The animal resulting from such methodology will include genetic material from the first and second organisms and thus be a "chimeric" organism. Provided that the cell expressing embryonic stem cell phenotype is genetically manipulated to include exogenous material the resulting chimeric will include that exogenous material within some, but not all of its cells.

The term "transgenic" is used to describe an animal which includes exogenous genetic material ("a transgene") within its cells. A transgenic animal is one that has an exogenous DNA sequence stably present in its cells.

The terms "polynucleotide," "nucleic acid," and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at the address made by placing "www." in front of and "/BLAST/" in back of "ncbi.nlm.nih.gov". Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. See *J. Mol. Biol.* 48: 443–453 (1970)

Of interest is the BestFit program using the local homology algorithm of Smith Waterman (Advances in Applied Mathematics 2: 482–489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127–149, 1988, Alan R. Liss, Inc. Percent sequence identity is calculated by FastDB based upon the following parameters:

| | |
|---|---|
| Mismatch Penalty: | 1.00; |
| Gap Penalty: | 1.00; |
| Gap Size Penalty: | 0.33; and |
| Joining Penalty: | 30.0. |

One parameter for determining percent sequence identity is the "percentage of the alignment region length" where the strongest alignment is found.

The percentage of the alignment region length is calculated by counting the number of residues of the individual sequence found in the region of strongest alignment. This number is divided by the total residue length of the target or query polynucleotide sequence to find a percentage. An example is shown below:

```
Target sequence:    GCGCGAAATACTCACTCGAGG
                      |   ||| ||||| |||
Query sequence:     TATAGCCCTAC.CACTAGAGTCC
                    1    5    10   15
```

The region of alignment begins at residue 9 and ends at residue 19. The total length of the target sequence is 20 residues. The percent of the alignment region length is 11 divided by 20 or 55%, for example.

Percent sequence identity is calculated by counting the number of residue matches between the target and query polynucleotide sequence and dividing total number of matches by the number of residues of the target or query sequence found in the region of strongest alignment. For the example above, the percent identity would be 10 matches divided by 11 residues, or approximately, 90.9%

The percent of the alignment region length is typically at least about 55% of total length of the sequence, more typically at least about 58%, and even more typically at least about 60% of the total residue length of the sequence. Usually, percent length of the alignment region can be as great as about 62%, more usually as great as about 64% and even more usually as great as about 66%.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate). Examples of low stringency conditions are hybridization and at temperature below about 50° C. and below about 6×SSC (0.9 M sodium chloride/0.09 M sodium citrate) and washing at below about 55° C. in 1×SSC (0.15 M sodium chloride/0.015 M sodium citrate). Stringent hybridization conditions also include conditions that are at least as stringent as the above specific representative conditions.

As used herein, an "endogenous" nucleic acid sequence is a nucleic acid sequence that is normally found in a cell. A "transgene" is a nucleic acid that is or has been introduced into a cell.

As used herein, the terms "predetermined endogenous DNA sequence" and "predetermined target sequence" refer to polynucleotide sequences contained in a pluripotent or totipotent cell used to make a transgenic non-human animal. Such sequences include, for example, chromosomal sequences (e.g., structural genes, promoters, enhancers, recombinatorial hotspots, repeat sequences, integrated proviral sequences), episomal sequences (e.g., replicable plasmids or viral replication intermediates), chloroplast and mitochondrial DNA sequences.

By "predetermined" it is meant that the target sequence may be selected at the discretion of the practitioner on the basis of known or predicted sequence information, and is not constrained to specific sites recognized by certain site-specific recombinases (e.g., FLP recombinase or CRE recombinase). In some embodiments, the predetermined endogenous DNA target sequence will be other than a naturally occurring germlne DNA sequence (e.g., a transgene, parasitic, or mycoplasmal or viral sequence).

DETAILED DESCRIPTION OF THE INVENTION

The present invention provides methods of producing transgenic livestock animals. The methods generally involve first introducing a nucleoprotein made up of nucleic acid and a recombinase into a totipotent or pluripotent cell to produce a recombinant totipotent or pluripotent cell and then growing the recombinant totipotent or pluripotent cell to produce the transgenic livestock animal. The invention further provides kits for use in generating transgenic non-human animals of the invention.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a transgene" includes a plurality of such transgene and reference to "the transgenic non-human animal" includes reference to one or more transgenic non-human animals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject methods of producing transgenic animals are described first in greater detail, followed by a review of representative applications in which the subject methods find use.

Methods of Producing Transgenic Livestock Animals

Transgenic non-human animals produced according to the subject invention are in many embodiments vertebrates, more specifically mammals and even more specifically livestock animals, e.g., an ungulate, such as an ovine (Sheep), porcine (Pigs), caprine (Goats), equine (Horse) or bovine (Ox, Cow, Buffalo) animal. In other embodiments, the transgenic animals may be fish, birds, etc. Transgenic animals according to many embodiments of the invention do not include small laboratory research animals, e.g., rodents, such as mice and rats.

The efficiency of generating a transgenic non-human animal is increased using the methods of the invention, e.g., the efficiency of generating a transgenic non-human animal is at least about 2-fold, at least about 3-fold, at least about 4-fold, at least about 5-fold, at least about 6-fold, at least about 7-fold, at least about 8-fold, at least about 9-fold, or at least about 10-fold higher when the transgene is coated with a recombinase before being introduced into the pluripotent or totipotent cell, as compared to the efficiency when the transgene is introduced into the pluripotent or totipotent cell in the absence of a recombinase. Thus, the efficiency of generating a transgenic non-human animal is at least about 2-fold, at least about 3-fold, at least about 4-fold, at least about 5-fold, at least about 6-fold, at least about 7-fold, at least about 8-fold, at least about 9-fold, or at least about 10-fold higher when the transgene is coated with a recombinase before being introduced into the pluripotent or totipotent cell, as compared to a control, where a control is the transgene in the absence of recombinase, e.g., as described in Example 1.

Using the methods of the invention, from about 10% to about 50%, from about 15% to about 40%, or from about 18% to about 36% of recombinant pluripotent or totipotent cells transferred into a pseudopregnant non-human animal develop into non-human animals that are transgenic.

Transgenes

Transgenes employed in the subject invention are produced using any known method, e.g., by chemical synthesis of oligonucleotides, nick-translation of a double-stranded DNA template, polymerase chain-reaction amplification of a sequence (or ligase chain reaction amplification), purification of prokaryotic or cloning vectors harboring a sequence of interest (e.g., a cloned cDNA or genomic clone, or portion thereof) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence.

Transgenes are generally single-stranded DNA (ssDNA) or double-stranded DNA (dsDNA). In some embodiments, transgenes contain 5' and/or 3' overhangs of from about 1 to about 10 bases. In other embodiments, transgenes have blunt ends. Transgenes are generally from about 50 to about 100, from about 100 to about 250, from about 250 to 500, from about 500 to about 1000, from about 1000 to about 5000, from about 5000 to about 10,000, from about 10,000 to about 20,000, or from about 20,000 to 50,000 nucleotides, or longer.

In certain embodiments of interest, the transgene has no significant homology to any endogenous nucleic acid sequences, e.g., the transgene has less than about 50%, less than about 45%, less than about 40%, less than about 35%, less than about 30%, less than about 25%, less than about 20%, less than about 15%, or less than about 10% nucleotide sequence homology with a stretch of nucleotides of similar length (e.g., a stretch of about 20, about 30, about 40, about 50, or more, contiguous nucleotides) of an endogenous sequence. A transgene having no significant homology to an endogenous nucleic acid sequence is also one that does not hybridize under stringent hybridization conditions to an endogenous nucleic acid sequence. In many of these embodiments, there is no "homology clamp" present in the transgene polynucleotide.

Thus, in certain embodiments, to achieve higher efficiency of generating a transgenic non-human animal, the transgene need not have any significant homology to any endogenous sequences. All that is required is that the transgene be introduced into the totipotent or pluripotent cell together with a recombinase.

In other embodiments, the transgene has one or more regions of homology to an endogenous nucleic acid sequence. The length of homology may be selected at the discretion of the practitioner on the basis of the sequence composition and complexity of the predetermined endogenous target DNA sequence(s) and guidance provided in the art. In these embodiments, transgenes have at least one sequence that substantially corresponds to, or is substantially complementary to, a predetermined endogenous DNA sequence (i.e., a DNA sequence of a polynucleotide located in a target cell, such as a chromosomal, mitochondrial, chloroplast, viral, episomal, or mycoplasmal polynucleotide). Such regions of homology serve as templates for homologous pairing with the predetermined endogenous sequence(s), and are also referred to herein as homology clamps.

If present, such homology clamps are typically located at or near the 5' or 3' end, and in some embodiments homology clamps are internally or located at each end of the polynucleotide (Berinstein et al. (1992) Molec. Cell. Biol. 12: 360, which is incorporated herein by reference). If present, the homology clamps are from about 12 to about 18, from about 18 to about 35, from about 35 to about 50, from about 50 to about 100, from about 100 to about 250, from about 250 to about 500, or from about 500 to about 1000, or more, bases in length. In these embodiments, transgenes have homology clamps that are highly homologous to the predetermined target endogenous DNA sequence(s).

The degree of sequence homology between the homology clamp (if present) and the targeted sequence and the base composition of the targeted sequence will determine the optimal and minimal clamp lengths (e.g., G-C rich sequences are typically more thermodynamically stable and will generally require shorter clamp length). If present, the homology clamp sequences contains at least about 90–95% sequence identity with the target sequence.

In some embodiments, where a homology clamp is present, the homology clamps flank a region of low (e.g., less than 50% nucleotide sequence identity) homology. For example, in some of these embodiments, a coding region that has low homology or no substantial homology to an endogenous nucleic acid sequence is flanked on the 5' and/or 3' ends of the coding region.

Recombinase Proteins

Recombinases suitable for use in the present invention are proteins that, when included with an exogenous transgene, provide a measurable increase in the recombination frequency between the transgene and an endogenous DNA sequence. Suitable recombinases are those that result in an increased efficiency of transgenic non-human animal production. In the present invention, "recombinase" refers to a family of RecA-like recombination proteins.

The best characterized recA protein is from *E. coli*, in addition to the wild-type protein a number of mutant recA-like proteins have been identified (e.g., recA803). Further, many organisms have recA-like recombinases with strand-transfer activities (e.g., Fugisawa et al., (1985) Nucl. Acids Res. 13: 7473; Hsieh et al., (1986) Cell 44: 885; Hsieh et al., (1989) J. Biol. Chem. 264: 5089; Fishel et al., (1988) Proc. Natl. Acad. Sci. USA 85: 3683; Cassuto et al., (1987) Mol. Gen. Genet. 208: 10; Ganea et al., (1987) Mol. Cell Biol. 7: 3124; Moore et al., (1990) J. Biol. Chem. 19: 11108; Keene et al., (1984) Nucl. Acids Res. 12: 3057; Kimiec, (1984) Cold Spring Harbor Symp. 48:675; Kimeic, (1986) Cell 44: 545; Kolodner et al., (1987) Proc. Natl. Acad. Sci. USA 84 :5560; Sugino et al., (1985) Proc. Natl. Acad, Sci. USA 85: 3683; Halbrook et al., (1989) J. Biol. Chem. 264: 21403; Eisen et al., (1988) Proc. Natl. Acad. Sci. USA 85: 7481; McCarthy et al., (1988) Proc. Natl. Acad. Sci. USA 85: 5854; Lowenhaupt et al., (1989) J. Biol. Chem. 264: 20568, which are incorporated herein by reference. See also Brendel et al. (1997) *J. Mol. Evol.* 44:528–541. Any known recombinase that increases the efficiency of transgenic non-human animal production is suitable for use in the present invention. Examples of such recombinase proteins include, for example but not limitation: recA, recA803, uvsX, and other recA mutants and recA-like recombinases (Roca, A. I. (1990) Crit. Rev. Biochem. Molec. Biol. 25: 415), sep1 (Kolodner et al. (1987) Proc. Natl. Acad. Sci. (U.S.A.) 84: 5560; Tishkoff et al. Molec. Cell. Biol. 11: 2593), RuvC (Dunderdale et al. (1991) Nature 354: 506), DST2, KEM1, XRN1 (Dykstra et al. (1991) Molec. Cell. Biol. 11: 2583), STPa/DST1 (Clark et al. (1991) Molec. Cell. Biol. 11: 2576), HPP-1 (Moore et al. (1991) Proc. Natl. Acad. Sci. (U.S.A.) 88: 9067), other eukaryotic recombinases (Bishop et al. (1992) Cell 69: 439; Shinohara et al. (1992) Cell 69: 457); incorporated herein by reference.

RecA may be purified from *E. coli* strains, such as *E. coli* strains JC12772 and JC15369 or similar strains. These strains contain the recA coding sequences on a "runaway" replicating plasmid vector present at a high copy numbers per cell. The recA803 protein is a high-activity mutant of wild-type recA. The art teaches several examples of recombinase proteins, for example, from *Drosophila*, yeast, plant, human, and non-human animalian cells, including proteins with biological properties similar to recA (i.e., recA-like recombinases).

In some embodiments, the recombinase is RAD51 or a functional homolog, variant, or derivative thereof. RAD51-encoding sequences are found in GenBank Accession Nos. D10023; X64270; and M88470. RAD51 homologs from species other than yeast can also be used. Baumann and West (1998) *TIBS* 23:247–251. RAD51 can be produced recombinantly, and purified according to well-established techniques. RAD 51 protein can also be purified from yeast. Methods of producing RAD51 are well known in the art. See, e.g., McIlwraith et al. (2000) *J. Mol. Biol.* 304:151–164; Kim et al. (2001) *J. Biochem.* 129:469–475; and Sugiyama et al. (1997) *J. Biol. Chem.* 272:7940–7945.

Recombinase protein(s) (prokaryotic or eukaryotic) are introduced into a totipotent or pluripotent cell simultaneously or contemporaneously (e.g. within about a few hours) with the trangene(s). Such administration is typically performed by microinjection, although electroporation, lipofection, and other transfection methods known in the art may also be used.

Alternatively, recombinase proteins may be produced in vivo from a heterologous expression cassette in a transfected cell or transgenic cell, such as a transgenic totipotent embryonal stem cell (e.g., a murine ES cell such as AB-1) used to generate a transgenic non-human animal line or a pluripotent hematopoietic stem cell for reconstituting all or part of the hematopoietic stem cell population of an individual. Conveniently, a heterologous expression cassette includes a modulatable promoter, such as an ecdysone-inducible promoter-enhancer combination, an estrogen-induced promoter-enhancer combination, a CMV promoter-enhancer, an insulin gene promoter, or other cell-type specific, developmental stage-specific, hormone-inducible, or other modulatable promoter construct so that expression of at least one species of recombinase protein from the cassette can by modulated for transiently producing recombinase(s) in vivo simultaneous or contemporaneous with introduction of a transgene into the cell. When a hormone-inducible promoter-enhancer combination is used, the cell must have the required hormone receptor present, either naturally or as a consequence of expression a co-transfected expression vector encoding such receptor.

Transgene/recombinase Mixtures

A mixture of a transgene and a recombinase is formed, and the mixture is introduced into a pluripotent or totipotent cell. Generally, the transgene is in an aqueous solution, which is generally buffered. In general, the transgene is a linear DNA molecule. Where the transgene is a ssDNA molecule, double-stranded transgene DNA is heat denatured (e.g, at 95° C.–100° C. for five minutes), then cooled to about 4° C. The recombinase is then added to the ssDNA or dsDNA. Additional components include, but are not limited to, ATPγS; RPA (Zaitseva et al. (1998) J. Biol. Chem. 274:2907–2915); and magnesium ions. Recombinase coating of transgene nucleic acid is initiated by incubating the transgene/recombinase mixture at 37° C for about 10 minutes.

Exemplary conditions used to coat a transgene with recA protein and ATPγS have been described. See U.S. Pat. Nos. 5,763,240; and 5,948,653, the disclosures of which are herein incorporated by reference. Transgenes can be coated using GTPγS, mixes of ATPγS with rATP and/or dATP, or dATP or rATP alone in the presence of an rATP generating system (Boehringer Mannheim). Various mixtures of GTPγS, ATPγS, ATP, ADP, dATP and/or rATP may be used, particularly preferred are mixes of ATPγS and ATP or ATPγS and ADP. Similar conditions are used to coat a transgene with other recombinases, such as RAD51. The following is a non-limiting example of a protocol for coating a polynucleotide with recA protein. This protocol is also used to coat a transgene polynucleotide with RAD51. Briefly, the transgene polynucleotide, whether double-stranded or single-stranded, is denatured by heating in an aqueous solution at 95–100° C. for five minutes, then placed in an ice bath for 20 seconds to about one minute followed by centrifugation for approximately 20 seconds, before use. When denatured transgene polynucleotides are not placed in a freezer at −20° C. they are usually immediately added to standard recA coating reaction buffer containing ATPγS, at room temperature, and to this is added the recA protein. Alternatively, recA protein may be included with the buffer components and ATPγS before the polynucleotides are added.

RecA protein concentration tested during reaction with polynucleotide varies depending upon polynucleotide size and the amount of added polynucleotide, and the ratio of recA molecule:nucleotide preferably ranges between about 3:1 and 1:3. When single-stranded polynucleotides are recA coated independently of their homologous polynucleotide strands, the mM and pM concentrations of ATPγS and recA, respectively, can be reduced to one-half those used with double-stranded targeting polynucleotides (i.e. recA and ATPγS concentration ratios are usually kept constant at a specific concentration of individual polynucleotide strand, depending on whether a single- or double-stranded polynucleotide is used). RecA protein coating of transgene polynucleotides is generally carried out in a standard 1×RecA coating reaction buffer. 10×RecA reaction buffer (i.e., 10×AC buffer) consists of: 100 mM Tris acetate (pH 7.5 at 37° C.), 20 mM magnesium acetate, 500 mM sodium acetate, 10 mM DTT, and 50% glycerol).

A reaction mixture typically contains the following components: (i) 2.4 mM ATPγS; and (ii) between 1–100 ng/μl of transgene. To this mixture is added about 1–20 μl of recombinase protein per 10–100 μl of reaction mixture, usually at about 5.2–11.0 mg/ml (purchased from a commercial source or purified), and is rapidly added and mixed. The final reaction volume for RecA coating of targeting polynucleotide is usually in the range of about 10–500 μl. RecA coating of transgene polynucleotide is usually initiated by incubating targeting polynucleotide-RecA mixtures at 37° C. for about 10–15 min. RecA protein concentrations in coating reactions vary, depending upon transgene size and the amount of added transgene: recA protein concentrations are typically in the range of 5 to 50 μM.

When single-stranded transgene polynucleotides are coated with recA, independently of their complementary strands, the concentrations of ATPγS and recA protein may optionally be reduced to about one-half of the concentrations used with double-stranded transgene polynucleotides of the same length: that is, the recA protein and ATPγS concentration ratios are generally kept constant for a given concentration of individual polynucleotide strands.

Another exemplary protocol is as follows. For single-stranded coated transgene DNA, linear, double-stranded DNA (200 ng) is heat denatured at 98° C. for 5 minutes, cooled on ice for 1 minute, and added to a protein coating mix containing tris-acetate buffer, 20 mM magnesium acetate, and 0.2–2.4 mM ATPγS. For the double-stranded transgene, linear double-stranded DNA (200 ng) is added directly to the protein coating mix. RecA or RAD51 is then immediately added, and the reaction place at 37° C. for 15 minutes. The magnesium acetate concentration is increased to a final concentration of 11 mM. RecA- or RAD51-coated ssDNA or dsDNA is diluted in tris-EDTA (10 mM Tris, 0.25 mM EDTA, pH 7.4) to a final concentration of 5 ng/μl and used for standard pronuclear microinjection of one-cell zygotes. Protein coating of transgene DNA is visualized by agarose gel electrophoresis with uncoated dsDNA as control. The electrophoretic mobility of protein-coated single- or double-stranded DNA is significantly retarded as compared with non-coated ssDNA or dsDNA.

The coating of transgene polynucleotides with recA protein can be evaluated in a number of ways. First, protein binding to DNA can be examined using band-shift gel assays (McEntee et al., (1981) J. Biol. Chem. 256:8835). Labeled polynucleotides can be coated with recA protein in the presence of ATPγS and the products of the coating reactions may be separated by agarose gel electrophoresis. Following incubation of recA protein with denatured duplex DNAs the recA protein effectively coats single-stranded transgene polynucleotides derived from denaturing a duplex DNA. As the ratio of recA protein monomers to nucleotides in the transgene polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to recA-binding to the transgene polynucleotide. Retardation of the coated polynucleotide's mobility reflects the saturation of targeting polynucleotide with recA protein. An excess of recA monomers to DNA nucleotides is required for efficient recA coating of short transgene polynucleotides (Leahy et al., (1986) J. Biol. Chem. 261:6954).

A second method for evaluating protein binding to DNA is in the use of nitrocellulose fiber binding assays (Leahy et al., (1986) J. Biol. Chem. 261:6954; Woodbury, et al., (1983) Biochemistry 22(20):4730–4737. The nitrocellulose filter binding method is particularly useful in determining the dissociation-rates for protein:DNA complexes using labeled DNA. In the filter binding assay, DNA:protein complexes are retained on a filter while free DNA passes through the filter. This assay method is more quantitative for dissociation-rate determinations because the separation of DNA:protein complexes from free transgene polynucleotide is very rapid.

The above produced recombinase coated transgenes, i.e., nucleoproteins made up of a recombinase and transgene polynucleotide, are then employed to produce transgenic animals, as described below.

Pluripotent and Totipotent Cells

The recombinase-coated transgene, i.e., nucleoprotein, is introduced into pluripotent or totipotent cells. Suitable pluripotent and totipotent cells include, but are not limited to, fertilized embryos at the pronuclear stage; embryonic stem cells; embryonic germ cells; embryonic inner cell mass cells; any somatic cell that can be used as a nuclear donor (e.g., differentiated embryonic and fetal cells; and including stably transfected somatic cells); and the like. Embryonic germ cells are described in, e.g., U.S. Pat. No. 6,194,635, the disclosure of which is herein incorporated by reference. Embryonic inner cell mass cells are described in, e.g., U.S. Pat. No. 6,107,543, the disclosure of which is herein incorporated by reference. In many embodiments, fertilized pronuclear stage embryos are used. Nuclear transfer from a somatic cell to a recipient oocyte, whose own genetic material has been removed, has been described. Wilmut et al. (1997) Nature 385:810–813.

Generation of Transgenic Animals

Transgenic animals are generated using well-established techniques. See, e.g. "Transgenic Animal Technology" C. A. Pinkert, ed. (1997) Acad. Press; "Transgenic Animals" F. Grosveld and G. Kollias, eds. (1997) Acad. Press; "Microinjection and Transgenesis: Strategies and Protocols" Cid-Arregui and Garcia-Carranca, eds. (1998) Springer-Verlag. See also, U.S. Pat. Nos. 6,268,545; 6,204,431; 6,222,094; and 6,255,554.

The recombinase-coated nucleic acid is transferred into the totipotent or pluripotent cell by well-known methods, depending on the type of cell. Suitable methods include, for example, microinjection, calcium phosphate treatment, electroporation, lipofection, and biolistics. Other methods used to include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference). Direct injection of DNA and/or recombinase-coated targeting polynucleotides into totipotent or pluripotent cells (e.g., in culture) may be used (Wolff et al. (1990) Science 247: 1465).

In some embodiments, the recombinase-coated transgene polynucleotide is introduced into a somatic cell, using any well-established technique. After integration into the genome of the somatic cell, nuclear transfer is used to transfer the nucleus of the somatic cell into a recipient oocyte, whose own genetic material has been removed. Nuclear transfer has been described. See, e.g., Wilmut et al. (1997) Nature 385:810–813; Campbell et al. (1996) Nature 380:64–66; and Schieke et al. (1997) Science 278:2130–2133.

Methods for generating transgenic fish have been described in the literature. See, e.g., U.S. Pat. Nos. 5,998,698; 5,998,697; and 5,545,808; Takeuchi et al. (2001) Mol. Reprod. Dev. 59:380–389; Guise et al. (1991) Biotechnol. 16:295–306; Liu et al. (1990) Biotechnol. 8:1268–1272; and Devlin et al. (2001) Nature 409:781–782.

In many embodiments, the transgene/recombinase mixture is introduced into a pluripotent or totipotent cell by pronuclear microinjection, using well-established techniques.

The resultant recombinant pluripotent/totipotent cell comprising the transgene is then grown to produce the desired transgenic animal. Any convenient protocol for growing the recombinant cell into a transgenic animal may be employed. In many embodiments, the recombinant totipotent or pluripotent cell is introduced into a pseudopregnant non-human animal where it is then allowed to develop into a transgenic, non-human animal. Such protocols are well known to those of skill in the art, and a representative specific protocols for both pigs and goats are provided in the Experimental Section, below.

The following is a non-limiting example of a method of generating a transgenic porcine. To generate a transgenic pig, embryos are recovered from the oviduct. They are placed into a 1.5 ml microfuge tube containing approximately 0.2–0.5 ml embryo transfer media (phosphate buffered saline +10% fetal calf serum, Gibco BRL). These are then centrifuged for approximately 5 minutes at 16,000×g RCF (13,450 RPM) in a microcentrifuge (Allied Instruments, model 235C). Embryos are removed from the microfuge tube with a drawn and polished Pasteur pipette and placed into a 35 mm petri dish for examination. If the cytoplasm is still opaque with lipid such that pronuclei are not visible, the embryos are centrifuged again for 3–6 minutes. Embryos to be microinjected are placed into a microdrop of media (approximately 100 μl) in the center of the lid of a 100 mm petri dish. Silicone oil is used to cover the microdrop and fill the lid to prevent media from evaporating. The petri dish lid containing the embryos is set onto an inverted microscope (Carl Zeiss) equipped with both a heated stage and Hoffman Modulation Contrast optics (200 times final magnification). A finely drawn (Kopf Vertical Pipette Puller, model 720) and polished (Narishige microforge, model MF-35) micropipette is used to stabilize the embryos while about 1–2 picoliters of transgene DNA solution containing approximately 200–500 copies of DNA construct is delivered into the male pronucleus with another finely drawn micropipette. Embryos surviving the microinjection process as judged by morphological observation are loaded into a polypropylene tube (2 mm ID) for transfer into the recipient pig.

Targeting of Endogenous DNA Sequences In Vivo

Generally, any predetermined endogenous DNA sequence can be altered by homologous recombination (which includes gene conversion) with an exogenous transgene (or complementary pair of transgenes) that has at least one homology clamp which substantially corresponds to or is substantially complementary to a predetermined endogenous DNA target sequence and which is introduced with a recombinase (e.g., recA) into a eukaryotic cell having the redetermined endogenous DNA sequence. Typically, a transgene polynucleotide (or complementary polynucleotide pair) has a portion having a sequence that is not present in the preselected endogenous targeted sequence(s) (i.e., a nonhomologous portion) which may be as small as a single mismatched nucleotide or may span up to about several kilobases or more of nonhomologous sequence. Generally, such nonhomologous portions are flanked on each side by homology clamps, although a single flanking homology clamp may be used.

Nonhomologous portions are used to make insertions, deletions, and/or replacements in a predetermined endogenous targeted DNA sequence, and/or to make single or multiple nucleotide substitutions in a predetermined endogenous target DNA sequence so that the resultant recombined sequence (i.e., a targeted recombinant endogenous sequence) incorporates some or all of the sequence information of the nonhomologous portion of the transgene polynucleotide(s). Additions and deletions may be as small as 1 nucleotide or may range up to about 2 to 10 kilobases or more.

In one application, a transgene can be used to repair a mutated sequence of a structural gene by replacing it or converting it to a wild-type sequence (e.g., a sequence encoding a protein with a wild-type biological activity). Genetic diseases can be corrected, either partially or totally, by replacing, inserting, and/or deleting sequence information in a disease allele using appropriately selected exogenous transgene polynucleotides.

Gene Inactivation

In addition to correcting disease alleles, exogenous transgene polynucleotides can be used to inactivate one or more genes in a cell (or transgenic nonhuman animal). Once the specific target genes to be modified are selected, their sequences will be scanned for possible disruption sites (convenient restriction sites, for example). Plasmids are engineered to contain an appropriately sized gene sequence with a deletion or insertion in the gene of interest and at least one flanking homology clamp which substantially corresponds or is substantially complementary to an endogenous target DNA sequence.

Vectors containing a transgene polynucleotide sequence are typically grown in $E.$ $coli$ and then isolated using standard molecular biology methods, or may be synthesized as oligonucleotides. Direct targeted inactivation which does not require vectors may also be performed. When using microinjection procedures one may use a transfection technique with linearized sequences containing only modified target gene sequence and without vector or selectable sequences. The modified gene site is such that a homologous recombinant between the exogenous transgene polynucleotide and the endogenous DNA target sequence can be identified by using carefully chosen primers and PCR, followed by analysis to detect if PCR products specific to the desired targeted event are present (Erlich et al., (1991) Science 252: 1643, which is incorporated herein by reference).

Utility

The methods of the invention are useful to generate transgenic, non-human animals, particularly livestock. Transgenic livestock can be generated that produce a protein not produced by wild-type livestock animals; that are knockouts, e.g., that no longer produce a particular protein; that correct a genetic defect in a livestock animal; or that produce more of a protein that they normally produce. Thus, for example, transgenic livestock can be generated that exhibit increase milk production; that produce milk with enhanced nutritional qualities; and the like. As one non-limiting example, β-lactoglobulin, which is a major allergen in cow milk for infants, can be knocked out, i.e., functionally disabled such that the transgenic livestock no longer produces β-lactoglobulin. Alternatively, a transgenic livestock animal can be generated wherein all or some of the endogenous β-lactoglobulin-coding sequences are replaced with a transgene that code for a protein that enhances the nutritional quality of the milk and/or enhances the quantity of milk produced and/or is beneficial to the transgenic livestock animal.

Kits

The invention further provides kits for practicing the invention. Kits include purified recombinase protein; and a buffer. In some embodiments, kits further include one or more transgenes, which are purified to a degree suitable for introduction into a pluripotent or totipotent cell. In other embodiments, a kit further includes materials needed for microinjection, e.g., a microinjection device, e.g., a microinjection pipette, and the like.

In many embodiments of the subject kits, the kits will further include instructions for practicing the subject methods or means for obtaining the same (e.g., a website URL directing the user to a webpage which provides the instructions), where these instructions are typically printed on a substrate, which substrate may be one or more of: a package insert, the packaging, reagent containers and the like.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXPERIMENTAL

Example I

Increased efficiency in the production of transgenic goats made by the pronuclear microinjection of cssDNA probes designed to alter the properties of milk and transgenic pigs made by the injection of a modified 1,3α-galactosyltransferase (GalT) gene.

1. Injection Material

Goats

All injection material (probes) was designed using goat β-lactoglobulin (β-Ig) sequences in combination with various inserted cDNAs. A 311 base pair (from −157 to +154) DNA fragment of the goat β-Ig gene was amplified from goat genomic DNA by polymerase chain reaction (PCR) with primers A (5'AAATGGTACCGGGGCCCGGGGAT-GAGCCAA3') (SEQ ID NO:01) and B (5'AAATTCTAGAT-GAGGCCCAGCTCCCCTGCC3') (SEQ ID NO:02) and cloned into pBluscript SK (Stratagene, La Jolla, Calif.) by the use of KpnI and XbaI sites included in the primers. The resulting plasmid (pBLG1) was then modified to replace the translation start codon in exon 1 with a 13 bp mutation sequence (GCGGCCGCTCGAG) (SEQ ID NO:03) containing the unique restriction enzyme sites XhoI and NotI by using PCR with primers A and F (5' GCGGCCGCTC- GAGGGCTGCAGCTGGGGTCGTG3') (SEQ ID NO:04) as well as B and E (5' CTCGAGCGGCCGCAAGTGCCTC-CTGCTTGCCCT3') (SEQ ID NO:05) for the first few cycles followed by amplification of the modified fragment with primers A and B. The resulting plasmid (pBlg-KO) contained 311 bp of goat β-Ig DNA surrounding the start codon that was replaced with the 13 bp mutation sequence. The introduction of the mutation also generated a 3 bp deletion resulting in a frame shift mutation in exon 1 of the goat β-Ig gene.

A total of five goat probes were generated in a similar fashion and ranged in size from 212–4736 bp (Table 1). All probes had the 13 bp XhoI, NotI mutation in place of the start codon. In addition, probe GHLZ had the complete 540 bp cDNA for human lysozyme inserted into the XhoI site in the plasmid pBlgKO. The cDNA for human lysozyme has XhoI ends and is described in Maga et al., 1994. Likewise, the KCN probes had the complete cDNA for bovine κ-casein (778 bp) inserted at the introduced XhoI site. The κ-casein cDNA was isolated from lactating bovine mammary tissue by standard RT-PCR methods with primers K1 (5'CTC-GAGATGATGAAGAGTTTTTTCCTAG3') (SEQ ID NO:06) and K3 (5'CTCGAGTTTATTATGCAGGAAT-CAA3') (SEQ ID NO:07). The orientation of the lysozyme and κ-casein inserts were verified by restriction enzyme digests, and the sequence of all injection material was verified by sequencing.

Pigs

The injection material used in pigs was designed using the catalytic coding domain of the pig GalT gene. The probes consisted of 150 bp each side of the catalytic coding domain present in exon 9 (from 547 to 834) with either a 19 bp (Pig1) or 50 bp (Pig2) mutation inserted at position 686 (Table 1).

TABLE 1 cssDNA Probes

| Probe | β-Ig or GalT regions used[a] | Inserted sequence[b] | Total length |
|---|---|---|---|
| BIgKOs | −101 to +101 | 13 bp mutation | 212 bp |
| BIgKOI | −157 to +153 | 13 bp mutation | 320 bp |
| GHLZ | −157 to +153 | 540 bp HLZ cDNA | 860 bp |
| KCNs | −641 to +639 | 778 bp KCN cDNA | 2068 bp |
| KCNI | −2002 to +1946 | 778 bp KCN cDNA | 4736 bp |
| Pig1 | −547 to +834 | 19 bp mutation | 304 bp |
| Pig2 | −547 to +834 | 48 bp mutation | 352 bp |

[a]Regions of DNA used in individual cssDNA probes either side of the start codon for the β-Ig gene in goats and either side of the catalytic coding domain in exon 9 in the pig GalT gene.
[b]Sequence inserted in each cssDNA probe.

The 19 bp mutation (TAGTGGATCCAGGCCTGTC) (SEQ ID NO:08) containing the unique restriction enzyme sites BamHI, StuI and SalI was introduced into exon 9 of the pig gene by PCR with primers GalT3 (5'GATA-GAGCTGGGTCCTCTGCG3') (SEQ ID NO:09) and Mut1 (5'CACGAGGTGTAGTGGATCCAGGCCTGTC-GACTTCCTCTTCTGCATTGACGTGGATC3') (SEQ ID NO:10) and GalT 4 (5'AATGTAGGCTGCGGACTC-CTTC3') (SEQ ID NO:11) and Mut2 (5'GAGGAA-GACGTCGACAGGCCTGGATCCACTACAC-CTCGTGCTGGATGTGGG3') (SEQ ID NO:12). The resulting 304 bp fragment was cloned into pBluescript and termed pPig1. Probe Pig2 was generated by digesting pPig1 with BamHI and StuI and introducing the 48 bp mutation (5'GGATCCGTTTTCCCAGTCACGACGCAT-GCCAGGAAACAGCTATGACAGGCCT3') (SEQ ID NO:13) consisting of BamHI and StuI ends and a unique SphI site flanked by the forward and reverse universal primers. Both probes were verified by restriction enzyme digests and DNA sequencing. All goat and pig DNA probes were used for RecA protein coating.

2. Conventional DNA Constructs

Non-RecA protein coated construct DNA ($\alpha_{s1}$-HLZ, 23.5 kb) consists of the promoter and flanking regions of the bovine $\alpha_{s1}$-casein gene with the cDNA for human lysozyme inserted in exon 1 of the casein gene as described in Maga, E. A., Anderson, G. B., Huang, M. C. and Murray, J. D. 1994. Expression of human lysozyme mRNA in the mammary gland of transgenic mice. Transgenic Res. 3,36–42. DNA construct Pig3 was an unrelated transgene.

3. Preparation of Injection DNA

All DNA probes and traditional DNA constructs were removed from vector sequences with appropriate restriction enzymes and purified with Elutip-D columns (Schleicher & Schuell, Keene, N. H.) prior to microinjection. For the RecA coating of cssDNA probes, linear, double-stranded DNA (200 ng) was heat denatured at 98° C. for 5 min, cooled on ice for 1 min and added to a protein coating mix containing tris-acetate buffer, 20 mM magnesium acetate and 0.2–2.4 mM ATPγS. RecA protein (Roche, Indianapolis, Ind.) was immediately added and the reaction placed at 37° C. for 15 min. The magnesium acetate concentration was then increased to a final concentration of 11 mM. The RecA protein coating of the cssDNA probe was visualized by agarose gel electrophoresis with uncoated double-stranded DNA as control as the electrophoretic mobility of RecA protein-coated single-stranded DNA is significantly retarded as compared with non-coated double stranded DNA. RecA-protein coated cssDNA was diluted to a concentration of 5 ng/μl and used for the standard pronuclear microinjection of one-cell goat or pig zygotes. The traditional DNA constructs $\alpha_{s1}$-HLZ and Pig3 DNA constructs were diluted to a final concentration of 5 ng/μl with microinjection buffer (10 mMTris, 0.25 mM EDTA pH7.4) for microinjection.

4. Generation of Embryos

Pronuclear stage goat embryos were obtained from donor animals in which estrus was synchronized by using progestin pessaries (Redopharm, Ltd.) for 14 days. On day 13, follicle stimulating hormone (FSH) was given twice daily (IM) over 3 days, beginning with a dose of 5 mg the first day, 4 mg the next day and 3 mg the third day if needed, with removal of the progestin sponge on day 14. Twenty-four hours after progestin removal, gonadotropin releasing hormone (GnRH Cystorelin[R], Walco Int'l.) was administered (5 mg dose, IV) to all animals, and does in estrus were bred to fertile bucks. Embryos were recovered by oviductal flushes on day 2, where day 0 is the first day of estrus. Estrus in recipient females was synchronized to correspond with the donors by use of progestin pessaries for 14 days. Microinjected embryos were surgically transferred into the oviducts of recipient does via midline laparotomy on the same day. Pregnancies were confirmed and monitored by ultrasound at days 28, 35, 47 and 54 following embryo transfer.

Pronuclear stage porcine embryos were obtained after injection of randomly selected periestrus gilts with PG600 (400 IU PMSG, 200 IU HCG, Intervet). Gilts were then grouped and sorted into new pens and feed changed from grower to sow diet. Seventy-three hours after PG600 administration, gilts were injected with 750 IU of HCG (Intervet). Gilts were bred with mixed semen 30 hours later. Pronuclear-stage embryos were collected from oviductal flushes 19–20 hours after breeding. Microinjected embryos were surgically transferred to recipient animals that were synchronized by weaning, on the same day. Pregnancies were confirmed by ultrasound. All animals were housed and cared for under AAALAC-approved conditions.

5. Analysis of Animals

Samples of umbilical cord were taken at birth, and ear notch (goats) or tail clips (pigs) were obtained within one week of age from all offspring. DNA was prepared from tissue samples by incubation in digestion buffer (0.05M Tris, 0.1M EDTA, 10% SDS and 20 mg/ml ProteinaseK) at 55° C. overnight followed by phenol chloroform extraction. Transgenic animals were initially identified by polymerase chain reaction (PCR) analysis. A PCR was first performed with an endogenous set of primers to serve as an internal PCR control (Table 2). For goats, the internal control amplified an endogenous 369 bp region spanning the start codon in exon 1 of the goat β-Ig gene. Similarly, in pigs the internal control amplified a 590 bp fragment in exon 9 of the porcine GalT gene (Table 2). All animals should have their respective PCR product.

To identify transgenic animals, PCR was performed in triplicate on each tissue sample with primer sets within each injected cssDNA probe (Table 2). For the BlgKO animals, a nested PCR was done first with primers flanking the mutation insertion site (C/D) followed by amplification with a mutation-specific primer (M2/D). Primers C/D generated a 202 bp fragment for all animals and a 111 bp product only if the animal was transgenic. For probe GHLZ and DNA construct $\alpha_{s1}$HLZ, a 243 bp product specific to the human lysozyme cDNA was amplified with primers HL3/HL4 if the animal was transgenic. These primers spanned exons in the human lysozyme cDNA. For probe KCN, a 585 bp product specific to the bovine κ-casein gene was amplified with primers K1 in exon 1 and K2 in exon 4. For the Pig1 and Pig2 probes, transgenic samples were identified by PCR with primers GalT3 and MR or Mut2, respectively, primers specific for the introduced mutation (164 bp). For all PCR, a total of 0.1 μg of genomic DNA was added to a standard PCR reaction containing buffer, 2.0 mM $MgCl_2$, 10 mM dNTP's, 10 pmol each of primer and 2.5 Units of taq DNA polymerase in a final volume of 50 μl. Samples were subjected to a single denaturation step of 97° C. for 2 min followed by 30–35 cycles of 94° C. for 1 min, annealing at 58° C. for 1 min and extension at 72° C. for 1 min. For probe KCN, the annealing temperature was 55° C. and for probe BlgKO, extension time was 30 sec. Products were analyzed by standard ethidium bromide agarose gel electrophoresis. PCR products from all positive animals were sequenced to verify the identity of the PCR product. Multiple PCR primer sets were run for each line of animals (data not shown).

Southern blots were performed on all PCR-positive animals as well as negative controls to verify further the presence of the injected DNA. Briefly, 15 μg of DNA was digested with TaqI overnight and run on a 1% gel overnight at 35V. Samples were transferred to a nylon membrane (Hybond +, Amersham Pharmacia) in 0.4N NaOH. Membranes were probed with the appropriate probe (human lysozyme cDNA for probe GHLZ and $\alpha_{s1}$HLZ; bovine κ-casein cDNA for probe KCN; injection material for probes BlgKO and Pig1 and 2) labeled by random priming with $^{32}P$. Hybidization and standard washes (0.1% SSC/0.1% SDS as final wash) were carried out at 65° C.

TABLE 2

PCR Analysis of Offspring

| Probe | Primer pair | Primer sequence | Target region |
|---|---|---|---|
| Goats | | | |
| Endogenous | G1/H1 | G1:5'AGGCCTCCTATTGTCCTCGT3'<br>H1:5'ACGTCACAGCCTCTCTTGGT3'<br>(SEQ ID NOS:14 & 15) | 369 bp in goat<br>β-lac exon 1 |
| BlgKO | C/D; M2/D | C:5'CCGGGCTGGCTGGCTGGCA3'<br>D:5'TCGAACCTTCTGGATGTCCAGG3'<br>M2:5'CAGCCCTCGAGCGGCCGC3'<br>(SEQ ID NOS:16, 17 & 18) | 202 bp & 111 bp<br>goat β-lac<br>exon 1 |
| GHLZ | HL3/HL4 | HL3a:5'TGGGAATGGATGGCTACAGG3'<br>HL4:5'CTCAAGCTACAGCATCAGCG3'<br>(SEQ ID NOS:19 & 20) | 243 bp in<br>human<br>lysozyme cDNA |
| KCN | K1/K2 | K1:5'CTCGAGATGATGAAGAGTTTTTT<br>CCTAG3'<br>K2:5'CTCGAGTTAGACCGCGGTTGAAGTA<br>A3' (SEQ ID NOS:21 & 22) | 585 bp exons<br>1 & 4 of bovine<br>κ-cn |
| Pigs | | | |
| Endogenous | GalT1/GalT2 | GalT1:5'GAGCATTACTTGGAGGAGTTC3'<br>GalT2:5'GCCTATATGATAATCCCAGCAG3'<br>(SEQ ID NOS:23 & 24) | 590 bp exon 9<br>pig GalT gene |
| Pig1 | GalT3/MR | GalT3:5'GATAGAGCTGGGTCCTCTGCG3'<br>MR:5'GACAGGCCTGGATCCACTA3'<br>(SEQ ID NOS:25 & 26) | 164 bp exon 9<br>pig GalT gene |
| Pig2 | GalT3/Mut2 | GalT3:5'GATAGAGCTGGGTCCTCTGCG3'<br>Mut2:5'GAGGAAGACGTCGACAGGCCTG<br>GATCCACTACACCTCGTGCTGGATGTGGG3'<br>(SEQ ID NOS:27 & 28) | 164 bp exon 9<br>pig GalT gene |

A total of 11 individual experiments were carried out, eight in goats and three in pigs, to evaluate the use of recombinase proteins in the efficiency of the production of transgenic livestock. Five different cssDNA probes were designed and generated and consisted of either a 13 bp mutation sequence (BIgKO), or the cDNAs for human lysozyme (GHLZ) or bovine κ-casein (KCN) flanked by varying amounts of goat β-Ig DNA (Table 1). Likewise in pigs, two different cssDNA probes (Pig1 and Pig2) were designed using the porcine GalT gene (Table 1). All cssDNA probes were successfully made into stable RecA protein-coated nucleoprotein filaments and used for the standard pronuclear microinjection of goat or porcine zygotes. The RecA-coating of the cssDNA was visualized by agarose gel electrophoresis (FIG. 1). A conventional DNA construct was also injected into goat embryos both in its conventional linear, double-stranded form and in the RecA protein-coated form. The conventional DNA construct Pig3 was unrelated to the pig cssDNA probes and was microinjected into porcine zygotes as linear double-stranded DNA. Results demonstrated that DNA ranging in size from 200–23,000 bp could be coated with RecA protein (data not shown).

The results of all experiments are presented in Table 3.

A pairwise comparison (Chi-square) demonstrated no significant difference between individual experiments of the same treatment. For instance, the results from cssDNA probes Pig1 and Pig2 were not significantly different from each other, nor were the results of probes BlgKO, GHLZ or KCN. Therefore, the RecA data from each species were pooled to conduct comparisons to non-RecA results.

The pregnancy rates for goats injected with RecA-coated cssDNA probes were consistent across all experiments at a mean of 71% (n=86, range of 67%–100% for individual probes). Pregnancy rates were not significantly different in goats when a conventional linear, double-stranded DNA construct without RecA was injected (51%). The pregnancy rates in pigs were lower than in goats but the same trend was observed. A mean of 41% (n=12, range 38% to 44%) of the pigs became pregnant after embryo transfer when RecA-coated css DNA was used and was not significantly different from the 29% rate obtained when a conventional double-stranded linear DNA construct without RecA was injected.

TABLE 3

Summary of RecA transgenic livestock production.

| DNA injected | No. embryos transferred | No. recipients | No. Pregnant (%)[1] | Embryo survival (%)[2] | No. transgenic (%)[3] | Transgene integration %[4] |
|---|---|---|---|---|---|---|
| PIGS | | | | | | |
| +RecA | | | | | | |
| Pig 1 | 378 | 16 | 7 (44) | 46 (12) | 14 (30) | 3.7 |
| Pig 2 | 423 | 13 | 5 (38) | 30 (7) | 7 (23) | 2.8 |
| Pig Total | 801 | 29 | 12 (41) | 76 (9.5) | 21 (28) | 3.25[a] |
| −RecA | | | | | | |
| Pig 3 | 358 | 14 | 4 (29) | 23 (6) | 1 (4) | 0.3[a] |
| GOATS | | | | | | |
| Probes | | | | | | |
| +RecA | | | | | | |
| BIgKO | | | | | | |
| 202 bp | 81 | 23 | 16 (69) | 26 (32) | 6 (23) | 7.4 |
| 310 bp | 12 | 4 | 4 (100) | 4 (33) | 3 (75) | 25 |
| Total | 93 | 27 | 20 (74) | 30 (32) | 9 (30) | 9.7 |
| GHLZ | 183 | 42 | 31 (71) | 58* (32) | 20 (34) | 10.9 |
| KCN | | | | | | |
| 640 bp | 97 | 21 | 14 (67) | 26 (27) | 9 (35) | 9.3 |
| 2000 bp | 142 | 31 | 21 (67) | 34 (24) | 6 (18) | 4.2 |
| Total | 239 | 52 | 35 (67) | 60* (25) | 15 (25) | 6.3 |
| Goat Total | 515 | 121 | 86 (71) | 148 (30)[b] | 44 (37) | 9.0[c] |
| −RecA | | | | | | |
| $\alpha_{s1}$-HLZ | 88 | 17 | 7 (40) | 15** (17)[b] | 1 (7) | 1.1[c] |
| Conventional | | | | | | |
| $\alpha_{s1}$-HLZ | | | | | | |
| +RecA | 47 | 9 | 6 (67) | 14 (30) | 5 (36) | 10.6[d] |
| −RecA | 42 | 8 | 5 (62) | 8 (19) | 1 (12) | 2.4[d] |

Values with the same superscripts are significantly different (P < 0.01)
[1]Percentage is the number of pregnant animals per number of recipients.
[2]Percentage is the number of offspring born per number of embryos transferred.
[3]Percentage is the number of transgenic animals per live births.
[4]Percent transgenic per number of embryos transferred.
*Three animals were born dead.
**One animal was born dead.

In goats, embryo survival, or the number of microinjected transferred embryos that resulted in the birth of an animal, was significantly greater (P<0.01) when RecA coated css DNA was used. A mean of 30% (n=148) of the microinjected, transferred embryos resulted in the birth of a kid compared with 17% (n=15) embryo survival when a conventional non-coated DNA construct was used. In pigs, the same trend was seen as more animals were born when RecA-coated DNA targeting probes were used (9.5%, n=76), although this was not significantly different from the embryo survival rate obtained when a conventional DNA construct was injected (6%, n=23, 0.1<P>0.05).

Animals were determined to be transgenic by PCR analysis of multiple tissue samples from all animals born. All samples were first screened with an endogenous set of primers (Table 2) as control for PCR amplification. The appropriate PCR product was observed for all samples analyzed (data not shown). A cssDNA probe-specific PCR with primers located in unique segments of the injection material (Table 3) was then performed on umbilical and ear (goats) or tail (pigs) DNA from all animals. Only transgenic animals that had incorporated the injected DNA somewhere in the genome would generate the appropriate PCR product (Table 2). Each sample was run in triplicate, and PCR products were sequenced to confirm identity of the amplified product. Results for each set of animals are shown in FIG. 2.

The PCR data demonstrated that the transgene integration frequency, or the number of animals that was transgenic per embryo microinjected, was affected by the use of RecA. A larger (P<0.01) number of founder animals were transgenic when RecA-coated cssDNA was used (Table 2). In goats, the transgene integration rate averaged 9% (range 4.2% to 25%) when RecA was used compared with 1.1% when the conventional double-stranded DNA construct without RecA was microinjected. Similarly, in pigs the transgene integration rate of 3.25% (range 2.8% to 3.7%) was higher (P<0.01) when RecA was used than when non-coated DNA was injected (0.3%). The same results were seen when a conventional DNA construct was microinjected coated and not coated with RecA (Table 2). An apparently higher but not significantly so, percentage of animals were born (30% coated, 19% non-coated) when RecA was used, and significantly more (P<0.01) of the animals (10.6% coated, 2.4% non-coated) were transgenic.

Figure 2A:
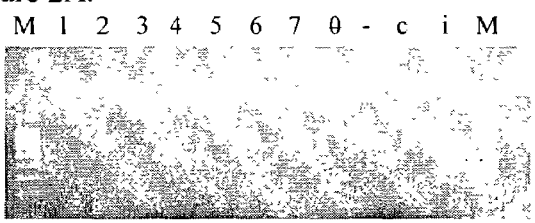
FIGS. 2A to 2D. PCR identification of transgenic animals. Lanes designated with M are 100 bp molecular weight marker, θ is a no DNA PCR control, – is the DNA from the uterus of a known negative embryo donor goat (A, C, and D) or pig (B), i is microinjection material, m is DNA from a human lysozyme transgenic mouse, + is DNA from a known positive transgenic goat made without RecA, c is genomic bovine DNA and u and e are the umbilical and ear tissue respectively of individual animals. Expected PCR sizes are given in FIGS. 1A and 1B.
Figure 2B:
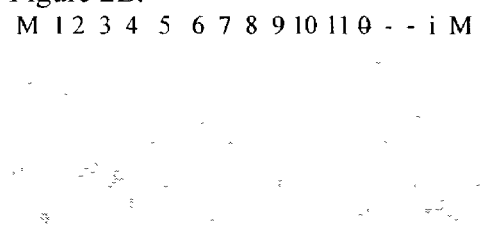
Figure 2C:
Figure 2D:
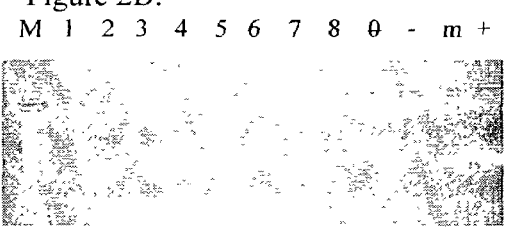
Figure 3:
FIG. 3. Southern blot of transgenic animals generated with and without RecA. 15 μg of genomic DNA was digested with TaqI to drop the human lysozyme cDNA (540 bp) from DNA targeting probe GHLZ and conventional DNA construct $\alpha_{s1}$-HLZ. Digested DNA was transferred to a nylon membrane and probed with a $^{32}$P-labelled complete cDNA for human lysozyme. Transgenic animals should have a 540 bp band corresponding to the human lysozyme cDNA. Lane 1 shows DNA from a non-transgenic animal. Lane 2 shows DNA from an $\alpha_{s1}$HLZ transgenic goat made by microinjection of conventional linear double stranded DNA. Lane 3 shows DNA from a GHLZ transgenic goat made by the microinjection of RecA protein-coated cssDNA.

The PCR results indicated that many of the founder animals generated with RecA were mosaic (FIG. 2a). The RecA-generated animals usually gave less consistent and weaker signals, indicative of being low-level mosaics, even within tissue type. The distribution of the transgene signal was more concentrated in the umbilical cord of the animals (data not shown). PCR results were further confirmed by Southern blotting (FIG. 3.). Clear Southern blots were more difficult to obtain for RecA-generated animals compared with those generated with a conventional DNA construct.

3. Discussion

The above results demonstrate that the use of RecA protein-coated cssDNA probes in the pronuclear microinjection of both goat and pig embryos resulted in a significant increase in both the embryo survival rate and transgene integration frequency. The standard pronuclear microinjection of embryos from both laboratory and livestock species results in a mean of 15% of the microinjected transferred embryos surviving to term (Wall, R. J. (1996). Transgenic livestock: Progress and prospects for the future. Theriogenology 45, 57–68). In these studies when RecA protein-coated DNA was microinjected, an embryo survival rate double the expected value with a mean of 30% of the transferred embryos in goats resulting in the birth of a kid was observed. The embryo survival rate was as expected in goats (16%) with the use of a non-RecA-coated DNA construct (Ebert, K. M. and Schindler, J. E. S. (1993). Transgenic farm animals: Progress report. Theriogenology 39, 121–135). The embryo survival rates seen in pigs were lower than the expected 15% when a conventional DNA construct was injected (6%) but higher when RecA was used (9.5%). The overall lower numbers seen with the pigs may be attributed to the fact that this species is one of the least efficient at transgenic animal production and that a fewer number of experiments were done. The increased embryo survival rates seen indicate that RecA may play some role in protecting the embryo from lysis after microinjection or in the types of holes that are left in the membrane after microinjection. The RecA may "mask" the injected DNA from the cell as foreign, thereby allowing the embryo to spend its energy repairing the holes made in the membrane and not trying to destroy the foreign DNA that has been introduced.

Transgene integration frequency has been found to be one of the main differences in the discrepancy in the efficiencies between laboratory animals and livestock. The proportion of animals that are born transgenic is much lower for livestock (Brem, G. B. (1985). Production of transgenic mice, rabbits and pigs by microinjection into pronuclei. Zuchthygiene 20, 251–252; Hammer, R. E., Pursel, V. G., Rexroad, C. E. Jr., Wall, R. J., Bolt, D. J., Ebert, K. M., Palmiter, R. D. and Brinster, R. L. (1985). Production of transgenic rabbits, sheep and pigs by microinjection. Nature 315, 680–683). Here, the transgene integration frequency was significantly increased in both goats and pigs when RecA protein-coated cssDNA was used, with 8× as many goats and 10× as many pigs being transgenic compared with the microinjection of a conventional DNA construct without RecA protein. This represents 10-fold increase (9.9 vs 0.99) in goats and a 3-fold increase (3.25 vs 0.9) in pigs in the efficiency of transgene integration over previously published reports on the standard pronuclear microinjection generation of transgenic livestock (Pinkert, C. A. and Murray, J. D. (1999). Transgenic Farm Animals. In, Transgenic Animals in Agriculture J. D. Murray, G. B. Anderson, A. M. Oberbauer and M. M. McGloughlin, eds. (CABI Publishing, New York, N.Y.) pp. 1–18). In a direct comparison with goats, one study reported 1.2 to 2.3% (mean =1.7%) of transferred, microinjected embryos born as transgenic kids (Ebert supra) compared with the presently observed 10% with RecA. The recombinase proteins may act by protecting the injected DNA from degradation by cellular enzymes and thereby increasing the chances and associations with the genome and a greater chance of producing a transgenic animal.

The sizes of the cssDNA probes used ranged from 212–4736 bp and were, in general, smaller than most conventional DNA constructs. However, reports using DNA constructs ranging in size from 2.3 to 26 kb in livestock (Ebert supra) and various sizes in mice (Brinster, R. L., Chen, H. Y., Trumbauer, M. E., Yagle, M. K. and Palmiter, R. D. (1985). Factors affecting the efficiency of introducing foreign DNA into mice by microinjecting eggs. Proc. Natl. Acad. Sci. 82, 4438–4442) have indicated that the length of the DNA injected does not significantly affect transgenesis. Due to the difficulty in working with livestock, it was not possible to directly compare the effect of the presence or absence RecA on all individual DNA probes. However, although the numbers were small, RecA did have an effect on the integration of a large conventional DNA construct. RecA coating of the 23 kb $\alpha_{s1}$HLZ DNA construct resulted in 5 transgenic founders, whereas only one founder was generated when the same DNA construct was injected without RecA.

Data collected by PCR analysis indicated that most founder animals were mosaic, even within tissue type, indicating that the recombinase reaction may require cell division and occur after the one-cell stage, thereby resulting in a mosaic animal. In general, 70% of founders are not mosaic and transmit their transgene to offspring (Wall, R. J. (2001). Pronuclear microinjection. Cloning and Stem Cells 3, 209–220). Our suspicions that many of our founders were mosaic were supported by the low intensity and differential tissue distribution of signals in our assays. The traditional approach to determine the level of mosaicism in an animal is by breeding and quantifying transmission of the transgene. Our goats are currently being bred to address this issue and determine if any is germ-line transgenic. To date, a total of 33 founder animals have been bred to produce 141 offspring, 23 of which were transgenic. Therefore, we estimate our level of mosaicism to be greater than the standard rate as only 16% of our F1 offspring were transgenic.

Other methods have been investigated to try to increase transgene integration frequency. The use of repetitive sequences of bovine satellite DNA resulted in a high frequency of transgene integration but also negatively affected embryo survival. (Rieth, A., Pothier, F., Gagne, M. and Sirard, M. A. (1999). Use of bovine satellite sequences to increase transgene integration by homologous recombination in bovine embryos. Mol. Reprod. Dev. 53, 1–7). The use of short interspersed elements (SINE) in mice resulted in a 4-fold increase in the integration frequency of a reporter gene (Kang, Y. K., Park, J. S., Lee, C. S., Yeom, Y. L., Han, Y. M., Chung, A. S. and Lee, K. K. (2000). Effect of short interspersed element sequences on the integration and expression of a reporter gene in the preimplantation-stage mouse embryos. Mol. Reprod. Dev. 56, 366–371). Three types of repetitive sequences, matrix attachment regions (MAR), SINE and microsatellites, were compared in one study, and none was found to increase the integration frequency over controls (Pintado, B. and Gutierrez-Adan, A. (2001). Effect of three types of repetitive sequences in mouse transgene integration. Theriogenology 55, 525). In all cases, work was carried out in embryos only; no live-offspring were produced. Restriction enzyme-mediated integration of transgenes has been demonstrated in one study in mice by co-injection of the restriction enzyme EcoRI along with the DNA construct. This approach was shown to double the transgene integration frequency (Seo, B. B., Kim, C. H., Yamanouchi, K., Takahashi, M., Sawasaki, T., Tachi, C. and Tojo, H. (2000). Co-injection of restriction enzyme with foreign DNA into the pronucleus for elevating production efficiencies of transgenic animals. Anim. Reprod. Sci. 63, 113–122). The use of RecA reported here not only had positive effects on embryo survival but also resulted in a greater increase in transgene integration frequency than published reports on the use of repetitive sequences or restriction enzymes. The presence of RecA protein may also help to promote homologous recombination. Experiments are underway to determine the site of integration of the probes.

The efficiency with which transgenic animals are generated by both pronuclear microinjection and NT-based cloning is quite low. The availability of a strategy that could be applied to the simple method of pronuclear microinjection to increase the efficiency of transgenic animal production, particularly in the more commercially important livestock species would be of great benefit. We have seen that the use of RecA protein increased embryo survival and enhanced the ability of the microinjected fragment to integrate into the host genome. Furthermore, the use of RecA can be easily applied to existing techniques and is applicable to any species.

The above results and discussion demonstrate that the use of RecA recombinase-coated DNA increases the efficiency of transgenic livestock production. The use of RecA results in a significant increase in both embryo survival rate and transgene integration frequency. For example, in the above specific examples, embryo survival rates were doubled in goats, and transgene integration was 10-fold higher in goats and 3-fold higher in pigs when RecA coating was used compared with use of a conventional DNA construct. The RecA coating of DNA is straightforward and can be applied to any species and any existing microinjection apparatus. This finding represents a significant improvement on a simple method that could make the production of transgenic livestock more efficient. As such, the present invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing a transgenic livestock mammal whose genome comprises a transgene, said method comprising: (a) introducing a nucleoprotein that comprises a transgene and a RecA or RAD51 recombinase into a pronuclear stage embryo of a livestock mammal and (b) transplanting said embryo into the oviduct of a pseudopregnant livestock mammal of the same species wherein the embryo develops to produce a transgenic livestock mammal whose genome comprises the transgene, wherein the transgene is randomly integrated into the genome.

2. The method according to claim 1, wherein said livestock mammal is an ungulate.

3. The method according to claim 2, wherein said ungulate is chosen from pigs, goats, sheep, cows and horses.

4. The method according to claim 3, wherein said ungulate is chosen from pigs and goats.

5. The method of claim 1, wherein said transgene of said nucleoprotein does not include a homology clamp.

6. The method according to claim 1, wherein said method has an efficiency of generation for said transgenic mammal that is at least two-fold higher as compared to the efficiency of generation of said transgenic mammal in the absence of a recombinase.

7. The method according to claim 1, wherein said transgene of said nucleoprotein is a double-stranded deoxyribonucleic acid.

8. The method according to claim 1, wherein said transgene of said nucleoprotein is a single-stranded deoxyribonucleic acid.

* * * * *